US005773211A

United States Patent [19]
Shih et al.

[11] Patent Number: 5,773,211
[45] Date of Patent: Jun. 30, 1998

[54] DIFFERENTIATION OF HTLV-I AND HTLV-II USING SYNTHETIC PEPTIDES

[75] Inventors: Jessie W. Shih, Lake Forest; John D. Burczak, Highland Park; Helen H. Lee, Lake Forest; Debra L. O'Donnell, Antioch, all of Ill.

[73] Assignee: Abbott Laboratories, Abbott Park, Ill.

[21] Appl. No.: 732,751

[22] Filed: Oct. 18, 1996

Related U.S. Application Data

[63] Continuation of Ser. No. 170,063, Dec. 20, 1993, abandoned, which is a continuation-in-part of Ser. No. 727,765, Jul. 10, 1991, abandoned.

[51] Int. Cl.[6] .......................... C12Q 1/70; G01N 33/569; G01N 33/574
[52] U.S. Cl. ............................ 435/5; 435/7.95; 436/518; 436/813
[58] Field of Search ....................... 435/5, 7.95; 436/518, 436/547, 813, 819

[56] References Cited

U.S. PATENT DOCUMENTS

| 4,525,300 | 6/1985 | Yoshida et al. . | |
|---|---|---|---|
| 4,689,398 | 8/1987 | Wu et al. . | |
| 4,804,746 | 2/1989 | Yoshida et al. . | |
| 5,003,043 | 3/1991 | Akita et al. | 530/324 |
| 5,017,687 | 5/1991 | Vahlne et al. | 530/324 |
| 5,156,949 | 10/1992 | Luciw et al. . | |
| 5,283,320 | 2/1994 | Vahine et al. | 530/325 |
| 5,359,029 | 10/1994 | Lacroix et al. | 530/300 |
| 5,378,805 | 1/1995 | Lal | 530/326 |

FOREIGN PATENT DOCUMENTS

| 0 267 622 A2 | 5/1988 | European Pat. Off. . |
|---|---|---|
| 0345792 | 12/1989 | European Pat. Off. . |
| 0346119 | 12/1989 | European Pat. Off. . |
| 439 077 A2 | 7/1991 | European Pat. Off. . |
| 0449116 | 10/1991 | European Pat. Off. . |
| WO 86/01834 | 3/1986 | WIPO . |
| WO 89/08664 | 9/1989 | WIPO . |
| WO 90/08162 | 7/1990 | WIPO . |
| WO 90/10231 | 9/1990 | WIPO . |
| WO 90/15820 | 12/1990 | WIPO . |
| WO 92/13946 | 8/1992 | WIPO . |
| WO 93 01316 | 1/1993 | WIPO . |
| WO 93/17341 | 9/1993 | WIPO . |
| WO 93/18054 | 9/1993 | WIPO . |

OTHER PUBLICATIONS

Lal et al., Serologic discrimination of human T-cell lymphotrophic virus infection by using a synthetic peptide-based enzyme immunoassay. Journal of Infectious Diseases 163:41–46, 1991.

U.S. application No. 06/664972, filed Oct. 26, 1984.

T.J. Palker et al., The Journal of Immunology, vol. 135, No. 1, pp. 247–254 (1965).

M. Seiki et al., *Proc. Natl. Acad. Sci USA*, "Human adult T-cell leukemia virus: Complete nucleotide sequence of the provirus genome integrated in leukemia cell DNA" Jun. 1983: vol. 80: 3618–3622.

K. Shimotohno et al., *Prod, Natl. Acad Sci USA,* "Complete nucleotide sequence of an infectious clone of human T-cell leukemia virus type II: An open reading frame for the protease gene" May 1985: vol. 82: 3101–3105.

T. J. Palker et al., *The Journal of Immunology*, "Mapping of Immunogenic Regions of Human T Cell Leukemia Virus Type I (HTLV–1) gp46 and gp21 Envelope Glycoproteins with Envencoded Synthetic Peptides and a Monoclonal Antibody to gp46[1]" Feb. 1, 1989: vol. 142: 971–978.

T. P. Hopp et al., *Roc. Natl. Acad. Sci USA*, "Prediction of protein antigenic determinants from amino acid sequences" Jun. 1981: vol. 78, 6 pp. 3824–3828.

*Primary Examiner*—Paula K. Hutzell
*Assistant Examiner*—Donna C. Wortman
*Attorney, Agent, or Firm*—Andreas M. Danckers

[57] ABSTRACT

Methods of differentiation of sera containing antibodies to HTLV-I from sera containing antibodies to HTLV-II are provided, along with peptides for their differentiation. Articles of manufacture containing these peptides are provided which allow for the differentiation of HTLV-I from HTLV-II infected sera.

17 Claims, No Drawings

DIFFERENTIATION OF HTLV-I AND HTLV-II USING SYNTHETIC PEPTIDES

This is a continuation application based on prior U.S. application Ser. No. 08/170,063, filed on Dec. 20, 1993, now abandoned, which was a continuation-in-part application based on prior U.S. application Ser. No. 07/727,765, filed on Jul. 10, 1991, now abandoned.

BACKGROUND OF THE INVENTION

This invention relates generally to a method for the detection of antibodies to Human T-Cell Lymphotropic Virus types I and II (HTLV-I and HTLV-II) in a test sample, and more particularly, relates to synthetic peptides specific for HTLV-I and HTLV-II, respectively, and methods useful for the differential detection of antibodies to HTLV-I and HTLV-II, thereby allowing the differential diagnosis of HTLV-I and HTLV-II infections.

HTLV-I is known to cause disease in humans, whereas HTLV-II is not clearly associated with disease. Epidemiological data indicate that approximately 50% of U.S. blood donors confirmed seropositive for HTLV-I are in fact infected with HTLV-II (Lee et al., unpublished observation). Therefore, there is a critical need to be able to distinguish between the two viruses for appropriate donor notification and counseling.

Current screening immunoassays for HTLV-I infection detect antibodies against HTLV-I and to a lesser extent HTLV-II. Serological methods which are more specific than EIA, such as Western blot (WB) and Radioimmunoprecipitation assays (RIPA), cannot distinguish between the two viruses.

To date, differentiation between HTLV-I and HTLV-II is achievable only by use of molecular genetic techniques such as restriction mapping or DNA sequencing of the provirus, and by Polymerase Chain Reaction (PCR) using specific primers for HTLV-I or HTLV-II. These procedures require the use of lymphocytes from patients to be tested which are clearly less convenient to collect and store than serum or plasma test samples. These techniques thus are limited in their usefulness in that they are time consuming, expensive, require specialized facilities and are not easily automated.

U.S. Pat. Nos. 4,525,300 and 4,804,476 to Yoshida teach methods for preparing antibodies to human leukemia virus related peptides. The antibodies disclosed are capable of binding to human leukemia virus.

Palker et al., *J. Immunol,* 135 (1):247–254 (1985) report the preparation of monoclonal antibodies reactive with HTLV-I which were raised to synthetic peptides representing sections of the p19 gag internal core protein. Some of the clones generated were reported to bind to HTLV-I virus isolates but not to bind to HTLV-II.

PCT Application No. PCT/US85/01803 to Slamon, published Mar. 27, 1986, teaches a method for the detection of antibodies HTLV-I and HTLV-II in samples by means of incubating samples with synthetic or cloned polypeptides and proteins derived from the HTLV genome and immobilized on a solid support. The teachings include methods for differentially diagnosing HTLV-I and HTLV-II, which require immunoprecipitation of proteins followed by molecular mass determination by methods such as SDS PAGE electrophoresis. However, SDS PAGE electrophoresis is not easily automated or convertible to a form suitable for routine laboratory use.

U.S. Pat. No. 4,689,398 to Wu teaches a further group of synthetic peptides, derived from the HTLV genome sequence, which may be used to detect antibodies specific to HTLV in test samples.

European Patent Application No. 0 267 622 to Masanori, published May 18, 1988, teaches a device comprising a fused HTLV qaq and env gene protein immobilized on a solid phase which may be used to detect antibodies to these proteins in a sample. However, this device is unable to distinguish between antibodies to HTLV-I and HTLV-II.

Palker et al. *J. Immunol,* 142:971–978 (1989) report the mapping of the immunogenic regions of the HTLV-I gp46 and gp21 env proteins and the synthesis of peptides which are useful in the generation of specific monoclonal antibodies. These peptides may be used in immunoassays to detect antibodies to HTLV. Additionally, the report suggests the presence of, but does not identify, a region of the gp46 protein which is not shared by HTLV-I and HTLV-II and may therefore be used to differentially detect antibodies to the two viruses.

PCT Publication No. WO89/08664 (PCT/SE89/00126) to Vahlne et al., published Sep. 21, 1989, teaches of further synthetic peptides, derived from the env region of the HTLV-I genome, which may be used in the detection of antibodies to the HTLV-I virus. No mention is made of differentiation between antibodies against HTLV-I and HTLV-II.

PCT Publication No. WO90/08162 to United Biomedical Inc., published Jul. 26, 1990, describes synthetic peptides for the detection of HTLV-I reactive antibodies and diagnosis of ATL (adult T cell leukemia/lymphoma). These peptides are from the transmembrane (p21e) and external (gp46) segments of the envelope protein of HTLV-I. Also described are immunoassays using these peptides. The peptide(s) described are used in the SynthEIA® (Olympus Corp., Lake Success, N.Y.) for HTLV-I.

PCT Publication No. WO90/10231 to Blomberg, published Mar. 5, 1990, teaches a method for differentially detecting antibodies to HTLV-I and HTLV-II by detecting binding of such antibodies to synthetic peptides derived from the gag and env regions of HTLV-I and HTLV-II. The method described requires the performance of at least four immunoassays on each sample and would therefore be inconvenient for the routine screening of a large number of samples. Peptides disclosed in Blomberg also show significant cross-reactivity. Blomberg improved the discrimination of infected sera by compiling all results and multiplying the absorbances with weights according to the relative ability of each peptide to discriminate between HTLV-I and HTLV-II. The weighted absorbances were then input into a computer program to calculate "points" for either HTLV-I or HTLV-II, respectively. According to Blomberg, using this serotyping technique, no false typing results were obtained, but a small number were found to be "not typable."

PCT Publication No. WO90/15820 to Vahlne et al., published Dec. 27, 1990, describes peptides and antibodies derived from the disclosed peptides which are immunologically reactive with HTLV-I specific antibodies. Several of the peptides are capable of distinguishing between HTLV-I and HTLV-II infection.

Recently, R. B. Lal et al. described the serologic discrimination of HTLV-I from HTLV-II using synthetic peptides which would be used to differentiate between HTLV-I and HTLV-II. R. B. Lal et al., *J. Infectious Diseases* 163:41–46 (January, 1991). In particular, they reported that HTLV-I "Env-5" (amino acids 242-257) represented an immunodominant domain of HTLV-I, and that ENV-5-based ELISA allowed distinction between HTLV-I and HTLV-II.

With the exception of this recent article and the two patent applications which describe differentiation (Vahlne, WO90/15820 and Blomberg, WO90/10231), all of the above disclosed techniques are aimed at the detection of specific antibodies to HTLV-I and HTLV-II. To date, however, no detailed methods have been described which would provide a simple method of effectively detecting, and distinguishing between, antibodies to HTLV-I and HTLV-II. In order to detect and distinguish between antibodies against HTLV-I And HTLV-II, unique antigenic determinants on the two viruses must Ye identified. Antigenic determinants on proteins have been predicted by the identification of hydrophilic regions using the method of Hopp and Woods, *Proc. Natl. Acad. Sci. U.S.A.* 78:3824 (1981) as well as identification of flexible regions using the method of Karplus and Schultz, *Naturwissenschaften* 72:212–213 (1985). Antigenic determinants appear to be located at hydrophilic as well as flexible regions of protein sequences. Antigenic determinants have also been empirically identified by immunological examination of peptides produced by protein degradation or in vitro synthesis.

Prior art methods for differentiating between HTLV-I infection and HTLV-II infection using peptide sequences from HTLV-I or HTLV-II have had the problem that HTLV-I derived peptides have been cross-reactive with sera infected with HTLV-II, and HTLV-II derived peptides have been cross-reactive with sera infected with HTLV-I. Prior art methods have also demonstrated significant sensitivity problems with respect to detecting antibody in sera. The present inventors believe that the addition or deletion of amino acids to a peptide significantly influences its ability to bind to antibodies. As a result, it is possible to significantly improve the performance of assays by altering the length of peptides from unique immunodominant regions of HTLV-I and HTLV-II. What were believed to be previously unknown antigenic regions as well as known antigenic regions were surveyed and systematically examined to identify peptide sequences which represent significant antigenic epitopes, which are strain specific between HTLV-I and HTLV-II and which show little cross-reactivity between strains.

SUMMARY OF THE INVENTION

It is an object of the present invention to provide a superior peptide assay for differentiating HTLV-I and HTLV-II.

It is another object of the present invention to provide an assay for differentiating HTLV-I and HTLV-II using peptides having increased selectivity and thus decreased cross-reactivity between HTLV-I and HTLV-II.

It is another object of the present invention to provide an assay for differentiating HTLV-I and HTLV-II which shows superior sensitivity for detecting antibody in sera.

It is yet another object of the present invention to provide a method which would be a useful tool to the physician, allowing a more detailed diagnosis of the disease and therefore more appropriate patient counseling and treatment.

It is yet another object of the present invention to provide a simple but reproducible HTLV-I and HTLV-II differentiation assay which facilitates routine laboratory usage and generates sensitive and specific results.

The amino acid sequences according to the present invention for the HTLV-I synthetic peptides were obtained from the predicted amino acid sequence as published by Seiki et al., *Proc. Natl. Acad. Sci. USA* 80:3618–3622 (1983). The peptides specific for HTLV-I include the following: HTLV-I env-1 (SEQ. ID. NO. 1), HTLV-I env-2 (SEQ. ID. NO. 2), HTLV-I env-3 (SEQ. ID. NO. 3), HTLV-I env-4 (SEQ. ID. NO. 4), HTLV-I env-5 (SEQ. ID. NO. 5), and HTLV-I env-6 (SEQ. ID. NO. 6). The peptides specific for HTLV-I further include HTLV-I gag-1 (SEQ. ID. NO. 7), HTLV-I gag-2 (SEQ. ID. NO. 8), HTLV-I gag-3 (SEQ. ID. NO. 9), HTLV-I gag-5 (SEQ. ID. NO. 10), HTLV-I gag-6 (SEQ. ID. NO. 11), and HTLV-I gag-7 (SEQ. ID. NO. 12).

The amino acid sequences according to the present invention for the HTLV-II synthetic peptides were obtained from the predicted amino acid sequences of the two HTLV-II prototypes. The amino acid sequence of the Mo HTLV-II was published by Shimotohno et al., *Proc. Natl. Acad. Sci. USA* 82:3101–3105 (1985). The sequence of the NRA HTLV-II prototype is unpublished data. The peptides specific for HTLV-II include the following: HTLV-II env-1 (SEQ. ID. NO. 13), HTLV-II env-1A (SEQ. ID. NO. 14), HTLV-II env-2 (SEQ. ID. NO. 15), HTLV-II env-2A (SEQ. ID. NO. 16), HTLV-II env-3 (SEQ. ID. NO. 17), HTLV-II env-4 (SEQ. ID. NO. 18), HTLV-II env-5 (SEQ. ID. NO. 19), HTLV-II env-5A (SEQ. ID. NO. 20), HTLV-II env-6 (SEQ. ID. NO. 21) and HTLV-II env-8 (SEQ. ID. NO. 22). The peptides specific for HTLV-II further include HTLV-II gag-2 (SEQ. ID. NO. 23), HTLV-II gag-3 (SEQ. ID. NO. 24), HTLV-II gag-4 (SEQ. ID. NO. 25). Peptides HTLV-II env-1A, HTLV-II env-2A, and HTLV-II env 5A are NRA sequences. All the other remaining HTLV-II sequences are Mo sequences.

According to the present invention, a method for differentiating antibodies against HTLV-I from antibodies against HTLV-II in a test sample is provided comprising: contacting the test sample with at least one peptide specific for HTLV-I to form a mixture, the peptide(s) specific for HTLV-I being selected from the group consisting of SEQ. ID. NO. 1, SEQ. ID. NO. 2, SEQ. ID. NO. 3, SEQ. ID. NO. 4, SEQ. ID. NO. 5, SEQ. ID. NO. 6, SEQ. ID. NO. 7, SEQ. ID. NO. 8, SEQ. ID. NO. 9, SEQ. ID. NO. 10, SEQ. ID. NO. 11 and SEQ. ID. NO. 12; incubating the mixture for a time and under conditions sufficient for antigen/antibody complexes to form; contacting the complexes with an indicator reagent comprising a signal generating compound attached to an anti-human IgG antibody to form a second mixture; incubating the second mixture for a time and under conditions sufficient for antigen/antibody/antibody complexes to form; and determining the presence of antibodies against HTLV-I by detecting the measurable signal.

In another embodiment of the invention, a method for differentiating antibodies against HTLV-I from antibodies against HTLV-II in a test sample is provided comprising: determining the presence of antibodies against HTLV-II in the test sample by contacting the test sample with at least one peptide specific for HTLV-II selected from the group consisting of SEQ. ID. NO. 13, SEQ. ID. NO. 14, SEQ. ID. NO. 15, SEQ. ID. NO. 16, SEQ. ID. NO. 17, SEQ. ID. NO. 18, SEQ. ID. NO. 19, SEQ. ID. NO. 20, SEQ. ID. NO. 21, SEQ. ID. NO. 22, SEQ. ID. NO. 23, SEQ. ID. NO. 24 and SEQ. ID. NO. 25 to form a mixture; incubating the mixture for a time and under conditions sufficient for antigen/antibody complexes to form; contacting the complexes with an indicator reagent comprising a signal generating compound attached to an anti-human IgG antibody, to form a second mixture; incubating said second mixture for a time and under conditions sufficient for antigen/antibody/antibody complexes to form; and determining the presence of antibodies against HTLV-II by detecting the measurable signal.

In a preferred embodiment of the invention, a first and a second assay are performed as above, the first assay comprising contacting a test sample with a peptide from HTLV-I according to the invention, and a second assay comprising contacting a test sample with a peptide from HTLV-II according to the invention.

A still more preferred embodiment of the invention comprises contacting said test sample with SEQ. ID. NO. 1 in the first assay, and contacting said test sample with one of SEQ. ID. NOS. 15 or 16 in the second assay.

A most preferred method according to the present invention provides for differentiation of HTLV-I and HTLV-II infected sera by performing two assays, as above, the first assay comprising contacting a test sample simultaneously with two peptides derived from HTLV-I, wherein the first peptide is chosen from the group consisting of SEQ. ID. NOS. 1, 2 and 6, and the second peptide is chosen from the group consisting of SEQ. ID. NOS. 3, 4 and 5. The second assay comprises simultaneously contacting the test sample with two peptides derived from HTLV-II, wherein the first peptide is chosen from the group consisting of SEQ. ID. NOS. 13, 14, 15 and 16 and the second peptide is SEQ. ID. NO. 22. Results from both assays are analyzed to determine the pattern of reaction of the test sample for antibodies against HTLV-I and HTLV-II to distinguish between HTLV-I and HTLV-II infections.

The invention also provides for an article of manufacture comprising packaging material containing a first and second container, the first container including a solid phase having attached thereto a peptide of the present invention specific for HTLV-I, and the second container including a solid phase having attached thereto a peptide of the present invention specific for HTLV-II, wherein the packaging material comprises a label on each of said containers which indicates that the contents thereof may be used to differentiate sera infected with HTLV-I from sera infected with HTLV-II.

The invention, together with further objects and attendant advantages, will best be understood by reference to the following description, examples and tables. However, the invention is not limited thereto.

DETAILED DESCRIPTION OF THE INVENTION

The present invention provides a method for the detection of antibodies against either HTLV-I or HTLV-II by means of detecting the binding of the antibodies to novel and unique synthetic peptides disclosed herein.

The present invention identifies novel and unique peptide sequences in regions of HTLV-I and HTLV-II which are useful in assays to detect and differentiate serum which contains antibodies to either of these viruses. For these purposes, unique peptide sequences are provided in several antigenic regions of HTLV-I env and gag that are specific for HTLV-I and do not significantly cross-react with sera having antibodies to HTLV-II. The amino acid sequence for the HTLV-I synthetic peptides were obtained from the predicted amino acid sequence as published by Seiki et al., *Proc. Nat'l. Acad. Sci. USA* 80:3618–22 (1983).

The present invention also identifies novel and unique peptide sequences in HTLV-II gp46 env and gag that are specific for HTLV-II and do not cross-react with serum having antibodies to HTLV-I. The amino acid sequences for the HTLV-II synthetic peptides were obtained from the predicted amino acid sequences of two HTLV-II prototypes, No and NRA. The amino acid sequence of the Mo HTLV-II prototype was published by Shimotohno et al., *Proc. Nat'l. Acad. Sci. USA* 82:3101–3105 (1985). The sequence of the NRA HTLV-II prototype is unpublished data, and is included in pending patent application Ser. No. 08/086,415 filed Jul. 1, 1993, assigned to Abbott Laboratories and the Regents of the University of California.

In general, the method of the invention comprises contacting a test sample with a solid phase to which at least one HTLV-I or at least one HTLV-II peptide is bound, to form a mixture. The mixture is incubated for a time and under conditions sufficient for antigen/antibody complexes to form. Then the complexes are contacted with an indicator reagent comprising an anti-human antibody attached to a signal generating compound, to form a second mixture. The second mixture is incubated for a time and under conditions sufficient to form antigen/antibody/antibody complexes. The presence of immobilized antibody is determined by detecting the measurable signal generated. The investigation of a test sample separately for antibodies against HTLV-I and antibodies against HTLV-II allows an effective method for distinguishing between infections with these two viruses.

The "solid phase" is not critical and may be any variety of materials which may be selected by one skilled in the art without undue experimentation. The term "solid phase" is used in a broad sense and refers to any material which is insoluble, or may be made insoluble by a subsequent reaction. Thus, porous or non-porous materials, latex or polystyrene particles, microparticles, beads, membranes, plastic tubes, walls of microtiter wells and tanned sheep red blood cells are all suitable examples. The size, dimensions, and shape of the solid phase are not generally critical in the methods of the invention. However, the present invention preferably envisions the use of microparticles when more than one peptide specific for HTLV-I or more than one peptide specific for HTLV-II is immobilized on a solid phase.

Suitable methods for immobilizing peptides on solid phases include ionic, hydrophobic, covalent interactions and the like. Those skilled in the art will recognize the scope of methodologies which may be applied relative to the application of useful solid phases. Linking agents known in the art may also be utilized to secure attachment of a peptide to the solid phase. The linking agent may be incorporated as part of, or derivatized onto, the solid phase before the peptides are added.

The "test sample" may be a sample of human or animal biological fluid, such as serum, plasma, ascites, urine, cerebral spinal fluid or any other body constituents, or any tissue culture supernatants which may contain antibodies of interest.

A suitable "indicator reagent" may be a signal generating compound (label) which is capable of generating a measurable signal detectable by external means conjugated (attached) to a specific binding member for antibodies derived from the test sample. In addition to being an antibody member of a specific binding pair for test sample-derived antibodies, the indicator reagent also may be a member of any specific binding pair, including either hapten-anti-hapten such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme and the like.

The various "signal generating compounds" (labels) contemplated include chromogens, catalysts such as enzymes, luminescent compounds such as fluorescein and rhodamine, chemiluminescent compounds, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

The reaction mixture is incubated for a time and under conditions sufficient for HTLV antigen/antibody complexes to form. Selecting appropriate times, temperature, and other conditions of the incubation are well within the skill in the art.

The methods employed in the description and examples described below were performed according to standard molecular genetics techniques known in the art, such as those described in Maniatis et al., *Molecular Cloning, A Laboratory Manual*, Cold Spring Harbor (1982). In one embodiment of the present invention, a synthetic peptide of the invention which is specific for antibodies against HTLV-I is immobilized on polystyrene beads. The beads are then incubated with a diluted test sample of human serum, plasma or other body fluid, and incubated under conditions and for an appropriate period of time during which time antibodies will bind specifically to the immobilized peptides on the bead. The bead then is washed to remove any unbound proteins which may be present. A second incubation then is performed in which the bead is incubated with an indicator reagent comprising anti-human antibodies labelled with an appropriate signal generating compound. By means of a suitable detection system, the amount of labelled anti-human antibody complex immobilized on the bead may be determined by measuring the detectable signal. Hence, the presence of specific antibodies against HTLV-I in the test sample is determined. The immunoassay is then repeated as stated above, except that a synthetic peptide according to the present invention which is specific for antibodies against HTLV-II is immobilized on the solid phase. A comparison of the pattern of reactivity of the test sample for antibodies against HTLV-I and antibodies against HTLV-II allows differentiation between infections with the two viruses.

In another embodiment, a synthetic peptide of the invention specific for HTLV-I is immobilized on polystyrene beads. The beads are then incubated with a test sample or a diluted test sample and an appropriate indicator reagent comprising a signal generating compound attached to anti-human IgG, under conditions and for an appropriate period of time to allow antibodies to bind specifically to the immobilized peptides on the bead and simultaneously to the indicator reagent. The amount of labelled anti-human antibody complex immobilized on the bead may be determined by detecting the measurable signal generated. Thus, the presence of antibodies against HTLV-I in the test sample may be determined by a single incubation. The immunoassay is then repeated, as stated above, with a synthetic peptide according to the invention which is specific for HTLV-II. A comparison of the pattern of reactivity of the test sample to antibodies against HTLV-I and antibodies against HTLV-II allows differentiation between infections with the two viruses.

In yet another embodiment, at least one of the synthetic peptides of the invention specific for antibodies against HTLV-I or at least one of the synthetic peptides of the invention specific for antibodies against HTLV-II, are immobilized on a nitrocellulose membrane. The peptide also may be conjugated or crosslinked to itself, other peptides or to various carrier proteins such as BSA, keyhole limpet hemocyanin, ovalbumin, and the like, before immobilization on the nitrocellulose membrane. The test sample is diluted and incubated on the membrane for a time and for conditions sufficient for antigen/antibody complexes to form. The membrane surface is then washed to remove unbound proteins, and in a second incubation, the membrane is incubated with an indicator reagent comprising anti-human antibodies labelled with a signal generating compound. The amount of labelled anti-human antibody immobilized on the membrane, and thus the presence of antibodies against either HTLV-I or HTLV-II, is determined by detecting the measurable signal generated with a suitable detection system. Quantification of the level of signal recognized by the detection system allows the quantification of the amount of specific antibody present in a test sample. A comparison of the pattern of reactivity of the test sample to antibodies against HTLV-I and antibodies against HTLV-II allows differentiation between infections with the two viruses.

In still another embodiment, a sandwich assay is utilized. This method comprises contacting a test sample with a solid phase to which at least one HTLV-I peptide or at least one HTLV-II peptide is bound to form a mixture. The mixture is incubated for a time and under conditions sufficient to allow antigen/antibody complexes to form. Then the complexes are contacted with antigen to which as been conjugated a signal generating compound, to form a second mixture. The second mixture is incubated and the presence of the antigen/antibody/antigen complex is determined by detecting the measurable signal generated. A comparison of the pattern of reactivity of the test sample for antibodies against HTLV-I and antibodies against HTLV-II allows differentiation between infections with the two viruses.

In still another embodiment, a combination of two peptides of the invention specific for HTLV-I are co-coated on a single solid support, for example, by immobilization on polystyrene beads. The procedure for co-coating of peptides is essentially the same as coating a single peptide, as described above, and in the examples, infra. Briefly, the peptides are individually dissolved into a stock solution at a suitable concentration. Aliquots of the two peptides are then added together into the coating solution for the beads. Preferably, the two peptides are added at equal concentrations, however, differing proportions of each peptide may also be used. The coated beads are then used in an immunoassay according to any of the above-methods. The procedure is then repeated with beads having co-coated thereon two peptides according to the invention which are specific for HTLV-II. A comparison of the pattern of reactivity of the test sample to antibodies against HTLV-I and antibodies against HTLV-II allows differentiation between infections with the two viruses.

A preferred embodiment comprises the use of two peptides specific for HTLV-I or two peptides specific for HTLV-II being bound to a microparticle solid phase. Microparticle EIA (MEIA) are preferably conducted with the use of polystyrene microparticles. The size of these particles is preferably between 0.19–5 microns. The protein may be bound either passively or actively on the particle. Passive coating is intended to mean non-covalent bonding or attachment between the peptide and the microparticle. An example of passive coating involves dissolving peptides in a stock solution with sterile water. The peptides are then diluted in a suitable coating buffer at twice the desired final coating concentration. The microparticles are washed and resuspended in a buffered salt coating solution. The microparticle and peptide solutions are mixed in equal proportions and incubated at a suitable temperature and length of time. At the end of the coating procedure, the coated microparticles are isolated by centrifugation, washed, and resuspended in a microparticle diluent. Due to the nature of the microparticle, the peptides become bound to the microparticle through electrostatic interactions or the like.

Active coating is intended to mean the effecting of a covalent bond between the peptide and the solid support. Generally, such a covalent bond is formed by either the carboxy or the amino terminal end of the peptide binding to an appropriate functional group on the surface of the microparticle. Microparticles having such functional groups are termed derivatized microparticles. An example of a derivatized microparticle has a carboxy functional group on its surface. The carboxy derivatized microparticle is then treated with 1-ethyl-3-(dimethyl-aminopropyl)carbodiimide hydrochloride (EDAC). Subsequently, the microparticle is processed in a similar fashion to the passively coated microparticle procedure except that the pH of the solution should be 4.5. The EDAC may be added to the final coating solution simultaneously with the peptides and microparticles, or to either the peptides or microparticles prior to mixing. The resulting coated microparticle has the peptides bound thereto because of reaction between the amino terminal ends of the peptides and the carboxy group on the microparticles. The use of EDAC with a non-derivatized microparticle will also result in an active coating.

Two approaches are envisioned for the use of microparticles coated with two peptide sequences in the same assay. First, the microparticles may be co-coated. In co-coating, the peptides are individually dissolved into a stock solution at a suitable concentration and subsequently added together. To the peptide mixture, the microparticles are added. Preferably, however, a first quantity of microparticles is coated with a first peptide sequence, and a second quantity of microparticles is coated with a second peptide sequence independently of each other. Subsequent to individual coating, the first and second quantity of coated microparticles are combined for use in an assay. This preferred technique facilitates quantification of the amount of each peptide actually present on the microparticle beads.

The methods of the present invention may be adapted for use in systems which utilize automated and semi-automated systems wherein the solid phase comprises a microparticle. Such systems include those described in pending U.S. patent application Ser. Nos. 425,651 and 425,643, which correspond to published EPO applications Nos. 0 425 633 and 0 424 634, respectively, which are incorporated herein by reference.

Other embodiments which utilize various other solid phases also are contemplated and are within the scope of this invention. For example, ion capture procedures for immobilizing an immobilizable reaction complex with a negatively charged polymer, described in co-pending U.S. patent application Ser. No. 150,278 corresponding to EPO publication 0 326 100, and U.S. patent application Ser. No. 375,029 (EPO publication 0 406 473) both of which enjoy common ownership and are incorporated herein by reference, may be employed according to the present invention to effect a fast solution-phase immunochemical reaction. An immobilizable immune complex is separated from the rest of the reaction mixture by ionic interactions between the negatively charged poly-anion/immune complex and the previously treated, positively charged porous matrix and detected by using various signal generating systems previously described, including those described in chemiluminescent signal measurements as described in co-pending U.S. patent application Ser. No. 921,979 corresponding to EPO Publication No. 0 273 115, which enjoys common ownership and which is incorporated herein by reference.

The use of scanning tunnelling microscopy for immunoassays also is a technology to which the methods of the present invention are easily adaptable. In scanning probe microscopy, in particular in atomic force microscopy, the capture phase, for example, a selected peptide or peptides of the invention, is adhered to a solid phase and a scanning probe microscope is utilized to detect antigen/antibody complexes which may be present on the surface of the solid phase. The use of scanning tunnelling microscopy eliminates the need for labels which normally must be utilized in many immunoassay systems to detect antigen/antibody complexes. Such a system is described in pending U.S. patent application Ser. No. 662,147, which enjoys common ownership and is incorporated herein by reference.

While the present invention discloses a preference for the use of solid phases, it is contemplated that the peptides of the present invention may be utilized in non-solid phase assay systems. These assay systems are known to those skilled in the art, and are considered to be within the scope of the present invention.

Another embodiment is envisioned in which only peptides specific for HTLV-I or peptides specific for HTLV-II are utilized in an immunoassay according to any of the methods described above. The specificity of the peptides disclosed herein, and the lack of cross-reactivity shown to be exhibited by these peptides, enables the use of these peptides in a single assay which will provide superior results. Thus, a single immunoassay using either one or more peptides according to the invention specific for HTLV-I or one of more peptides according to the invention specific for HTLV-II, results in increased specificity and selectivity with respect to infection by either HTLV-I or HTLV-II. However, because of the superior differentiation results obtained, it is preferred that two assays be performed, a first assay utilizing one or more peptides specific for HTLV-I and a second assay utilizing one or more peptides specific for HTLV-II, when differentiating between sera infected with HTLV-I or HTLV-II.

Accordingly, tests which detect specific antibodies against HTLV-I separately from antibodies against HTLV-II may be designed by selecting appropriate synthetic peptides of each of these viruses, and coating them onto solid phases, thereby facilitating the differential diagnosis of the two viral infections. Peptides suitable for the specific detection of antibodies against HTLV-I are specified herein and comprise the peptides of the HTLV-I env region and the peptides of the HTLV-I gag region which are designated as SEQ. ID. NO. 1 through SEQ. ID. NO. 12. Peptides suitable for the specific detection of antibodies against HTLV-II also are specified herein and comprise the peptides of the HTLV-II env region, and the peptides of the HTLV-II gag region, and are designated as SEQ. ID. NO. 13 through SEQ. ID. NO. 25.

It is contemplated that the reagent employed for the assay may be provided in the form of a kit with one or more containers such as vials or bottles. Each container or vial contains a separate reagent such as a diluent, indicator reagent, signal generating compound, assay reagents comprising at least one peptide of the present invention, and the like. The kit would also include instructions which indicate that the contents thereof may be used to differentiate between HTLV-I and HTLV-II infection.

The following examples and related tables are intended to further illustrate the invention. It will be understood, however, that the invention is not limited to these specific examples or the embodiments expressed therein.

EXAMPLES

Example 1

Detection of Antibodies against HTLV-I

Reagents

Peptides were synthesized by stepwise addition of amino acids to a solid phase using procedures known in the art and described in Merrifield *J. Am. Chem Soc* 85:2149–2154

(1963) and Barany and Merrifield in E. Gross and J. Meienhofer, eds., *The Peptides*, Vol. 2:1–284 (1979), Academic Press, New York, which are incorporated herein by reference. Briefly, the procedure was as follows. The synthesis was performed starting with the C terminus and progressing to the N terminus. N-protected amino acids were used, with N being t-butyloxycarbonyl (t-Boc). The C terminum t-Boc amino acid was attached to the solid phase. The t-Boc protecting group was removed with trifluoroacetic acid, leaving a free amino group to couple to the next amino acid. Successive t-Boc amino acids were added, coupled using a reagent such as DCC (N-N'-dicyclohexylcarbodiimide) and then deprotected. Once the peptide was completed, the final t-Boc protecting group was removed and the peptide was cleaved from the polymer by using anhydrous hydrogen fluoride.

Peptides prepared as described hereinabove were coated on a polystyrene bead solid support for capture of antibodies against HTLV-I using procedures known in the art. Briefly, the polystyrene beads were washed with distilled water and incubated at 40° C. for two (2) hours with between 0.01 µg/ml and 50 µg/ml of peptide(s) in a phosphate buffered saline (PBS) solution. The beads were washed once with PBS containing 0.1% Triton X-100® for one (1) hour, blocked for one (1) hour with 2% bovine serum albumin (BSA) in PBS, overcoated with 5% sucrose in PBS for 15 minutes, and then dried.

Beads used in this example as the solid phase for the detection of antibodies to HTLV-I were coated with peptide HTLV-I env-1 (SEQ. ID. NO. 1) corresponding to amino acids 174-204.

Anti-human IgG antiserum was prepared by immunizing goats with purified human IgG, according to known methods. The resulting antiserum was affinity purified and labelled with Horseradish Peroxidase (HRPO).

Method

Samples were diluted in sample diluent buffer between dilution factors of 1:2 and 1:1000. 200 µl of the diluted sample was incubated with a coated bead in a reaction tray for 60 minutes at 40° C. After thorough washing, the beads were incubated with goat anti-human HRPO diluted in a suitable diluent, for 30 minutes at 40° C. The beads were again thoroughly washed. The amount of HRPO immobilized on the beads was quantified by incubating with an O-phenylenediamine:2HCl (OPD) reagent for 30 minutes at ambient room temperature. At the end of this incubation 1.0 ml of 1N sulfuric acid was added to stop the color generating reaction. The degree of color generation was determined by measuring the absorbance of the resulting solution at 492/600 nm.

Results

The method of the invention was applied to a panel of 100 test samples that previously had been confirmed to be positive for antibodies against HTLV by the method of D. W. Anderson et al., *Blood* 74:2585–91 (1989), with 50 samples confirmed positive for HTLV-I and 50 samples confirmed positive for HTLV-II by Polymerase Chain Reaction (PCR). The method of the invention detected 48 of 50 (96%) samples positive for antibodies against HTLV-I. Additionally, no significant cross-reactivity was detected with the 50 samples of HTLV-II infected sera.

Example 2

Detection of Antibodies against HTLV-II

Reagents

Peptides prepared as described hereinabove in Example 1 were coated on polystyrene beads as the solid phase for capture of antibodies against HTLV-II, as follows. The polystyrene beads were washed with 15% v/v isopropanol and incubated at 40° C. for two (2) hours with between 0.01 µg/ml and 50 µg/ml of peptide(s) in a PBS solution. The beads were washed once with PBS containing 0.15% Triton X-100® for one (1) hour and blocked for one (1) hour with 2% BSA in PBS, then overcoated with 5% sucrose in PBS for 20 minutes at room temperature and then dried.

For the detection of antibodies against HTLV-II in this example, beads were coated with peptide HTLV-II env-2 (SEQ. ID. NO. 15) corresponding to amino acids 171–198 of the HTLV-II gp46 env protein.

Anti-human IgG antiserum was prepared by immunizing goats with purified human IgG. The resulting antiserum was affinity purified and labelled with HRPO according to standard methods known in the art.

Method

Samples were diluted in sample diluent buffer between a dilution factor of 1:2 and 1:1000. 200 µl of the diluted sample was incubated with a coated bead in a reaction tray for 60 minutes at 40° C. After thorough washing, the beads were incubated for 30 minutes at 40° C. with goat anti-human HRPO diluted in a suitable diluent. The beads were again thoroughly washed. The amount of HRPO immobilized on the beads was quantified by incubating with an OPD reagent for 30 minutes at ambient room temperature. At the end of this incubation 1.0 ml of 1N sulfuric acid was added to stop the color generating reaction. The degree of color generation was determined by measuring the absorbance of the substrate at 492/600 nm.

Results

When this method was applied to a panel of test samples which had been confirmed to be positive for antibodies against HTLV by the method of Anderson (cited supra) and positive for HTLV-II by PCR, the test was able to detect 72 of 74 samples (97.3%). Additionally, when tested against 50 samples confirmed positive for HTLV-I, cross-reactivity was detected for only 1 sample. This sample, however, was also borderline HTLV-II positive.

Example 3

Reactivity Of Peptides With HTLV-I And HTLV-II Infected Sera

Reagents were prepared as for example 2 except that peptides for SEQ. ID. NO. 1 through SEQ. ID. NO. 25 were individually coated onto beads. The data presented below in Table 1 is a compilation of the data generated for a panel of 28 confirmed HTLV positive samples. 14 of the samples were confirmed HTLV-I positive and the other 14 samples were confirmed HTLV-II positive. The corresponding designation of the SEQ. ID. NO. is indicated in parenthesis.

As shown in Table 1, no cross-reactivity was observed with HTLV-II sera for any of the peptides specific for HTLV-I, and no significant cross-reactivity was observed for HTLV-I sera with peptides specific for HTLV-II.

TABLE 1

Reactivity Of Individual Peptides

| Peptide | Amino Acid | HTLV-I Reactivity | HTLV-II Reactivity |
| --- | --- | --- | --- |
| SEQ. ID. 1 (HTLV-I env-1) | 174–204 | 11/14 | 0/14 |
| SEQ. ID. 2 (HTLV-I env-2) | 180–213 | 10/14 | 0/14 |
| SEQ. ID. 3 (HTLV-I env-3) | 227–257 | 7/14 | 0/14 |

TABLE 1-continued

Reactivity Of Individual Peptides

| Peptide | Amino Acid | HTLV-I Reactivity | HTLV-II Reactivity |
|---|---|---|---|
| SEQ. ID. 4 (HTLV-I env-4) | 230–260 | 12/14 | 0/14 |
| SEQ. ID. 5 (HTLV-I env-5) | 237–260 | 9/14 | 0/14 |
| SEQ. ID. 6 (HTLV-I env-6) | 190–213 | 4/14 | 0/14 |
| SEQ. ID. 7 (HTLV-I gag-1) | 100–129 | 14/14 | 0/14 |
| SEQ. ID. 8 (HTLV-I gag-2) | 104–129 | 14/14 | 0/14 |
| SEQ. ID. 9 (HTLV-I gag-3) | 109–129 | 5/14 | 0/14 |
| SEQ. ID. 10 (HTLV-I gag-5) | 100–119 | 10/14 | 0/14 |
| SEQ. ID. 11 (HTLV-I gag-6) | 100–127 | 13/14 | 0/14 |
| SEQ. ID. 12 (HTLV-I gag-7) | 100–126 | 13/14 | 0/14 |
| SEQ. ID. 13 (HTLV-II env-1) | 167–198 | 0/14 | 9/14 |
| SEQ. ID. 14 (HTLV-II env-1A)* | 167–198 | 0/14 | 9/14 |
| SEQ. ID. 15 (HTLV-II env-2) | 171–198 | 0/14 | 11/14 |
| SEQ. ID. 16 (HTLV-II env-2A)* | 171–198 | 0/14 | 12/14 |
| SEQ. ID. 17 (HTLV-II env-3) | 173–200 | 0/14 | 7/14 |
| SEQ. ID. 18 (HTLV-II env-4) | 173–204 | 0/14 | 8/14 |
| SEQ. ID. 19 (HTLV-II env-5) | 176–209 | 0/14 | 8/14 |
| SEQ. ID. 20 (HTLV-II env-5A)* | 176–209 | 0/14 | 8/14 |
| SEQ. ID. 21 (HTLV-II env-6) | 228–257 | 0/14 | 3/14 |
| SEQ. ID. 22 (HTLV-II env-8) | 83–108 | 0/14 | 6/14 |
| SEQ. ID. 23 (HTLV-II gag-2) | 111–129 | 0/14 | 4/14 |
| SEQ. ID. 24 (HTLV-II gag-3) | 109–127 | 0/14 | 5/14 |
| SEQ. ID. 25 (HTLV-II gag-4) | 107–125 | 0/14 | 3/14 |

*These three sequences were derived from the NRA HTLV-II prototype.

Example 4

Detection Of Antibodies Against HTLV-I And HTLV-II Using Co-Coated Beads

Trial A

Using the procedure as described in Example 1, beads were co-coated with a solution containing a mixture of peptides according to the invention specific for HTLV-I. By co-coating beads, the present inventors discovered that it was possible to increase the sensitivity of the assay to detect either HTLV-I or HTLV-II, while maintaining the level of selectivity against cross-reactivity. For example, antibodies in a given test sample may be detected by one peptide, but not by another peptide. The same two peptides, however, may give the opposite results for another sample. Thus, a co-coated bead with both peptides would detect antibodies in both samples. For this assay, the peptides were coated as in Example 1, except that the peptide coating solution included equal concentrations of SEQ. ID. NOS. 2 and 5. An assay was conducted using the same panel of 28 sera samples as in Example 3. As illustrated in Table 2, when applied to the 28 member panel, the method of the invention was able to correctly identify 14 out of 14 (100%) of the samples positive for HTLV-I, with no significant cross reactivity for 14 samples positive for HTLV-II. Similar results were obtained for assays run with combinations of SEQ. ID. NOS. 1 and 4, and SEQ. ID. NOS. 2 and 5.

Using the procedure described in Example 1, peptides prepared as described above which were specific for HTLV-II were co-coated on polystyrene beads. Peptide combinations used were SEQ. ID. NOS. 15 and 13, SEQ. ID. NOS. 15 and 14, SEQ. ID. NOS. 15 and 18, SEQ. ID. NOS. 15 and 19, SEQ. ID. NOS. 15 and 21, and SEQ. ID. NOS. 15 and 22. Results are tabulated in Table 2. As shown in Table 2, assays run with a combination of HTLV-II specific peptides showed no significant cross-reactivity with samples confirmed positive for HTLV-I, and excellent results with respect to detection of HTLV-II.

TABLE 2

Differentiation Of HTLV-I And HTLV-II With Co-Coated Beads

| Peptides | HTLV-I Reactivity | HTLV-II Reactivity |
|---|---|---|
| SEQ. ID. NOS. 1 and 4 | 14/14 | 0/14 |
| SEQ. ID. NOS. 1 and 5 | 14/14 | 0/14 |
| SEQ. ID. NOS. 2 and 5 | 14/14 | 0/14 |
| SEQ. ID. NOS. 15 and 13 | 0/14 | 11/14 |
| SEQ. ID. NOS. 15 and 14 | 0/14 | 9/14 |
| SEQ. ID. NOS. 15 and 18 | 0/14 | 11/14 |
| SEQ. ID. NOS. 15 and 19 | 0/14 | 7/14 |
| SEQ. ID. NOS. 15 and 21 | 0/14 | 11/14 |
| SEQ. ID. NOS. 15 and 22 | 0/14 | 8/14 |

Trial B

An assay using co-coated beads was prepared for additional sample testing. Peptides prepared according to the present invention were coated on polystyrene beads as the solid support for the capture of antibodies against HTLV-II using procedures known in the art. Polystyrene beads were prepared by washing with 15% N-propyl alcohol and incubated at 40° C. for two hours with between 0.01 μg/ml and 50 μg/ml of peptide in a phosphate buffered solution. The beads were washed once with PBS containing 0.15% Triton X-100 for one hour at 40° C. and blocked for one hour at 40° C. with 2% BSA in PBS, and then overcoated with 5% sucrose in PBS for 20 minutes at room temperature. The beads are then drained and dried with nitrogen gas heated to 37° C. until dry, approximately one to two hours. The beads are stored desiccated at 2°–8° C. until use.

For detection of antibodies against HTLV-II in this example, beads were co-coated with peptides according to SEQ. ID. NOS. 15 and 22 at equal concentrations. Antihuman IgG antiserum was prepared by immunizing goats with purified human IgG. The resulting antiserum was affinity purified and labeled with HRPO according to standard methods. A similar assay was performed using polystyrene beads co-coated with SEQ. ID. NOS. 1 and 5.

Results

Beads prepared according to the method of this example were used in an immunoassay against a panel of 100 test samples which had been confirmed positive for HTLV by the method of Anderson, supra, with 50 samples confirmed positive for HTLV-I and 50 samples confirmed positive for HTLV-II by PCR. In that assay, the beads coated with SEQ. ID. NOS. 15 and 22 correctly identified 47 out of 50 samples as HTLV-II positive. Additionally, in this immunoassay, the beads showed no significant cross-reactivity with sera samples confirmed positive for HTLV-I.

For the assay performed utilizing beads co-coated with SEQ. ID. NOS. 2 and 5, 55 of 57 samples confirmed positive for HTLV-I were detected, with no significant crossreactivity for HTLV-II infected sera.

Example 5

Effect of Peptide Sequence on Assay Performance

Reagents were prepared as for example 1 except that beads were coated individually with HTLV-I env-1 (SEQ. ID. NO. 1) (174-204), HTLV-I env-6 (SEQ. ID. NO. 6) (190-213), HTLV-I gag-1 (SEQ. ID. NO. 7) (100-129), HTLV-I gag-3 (SEQ. ID. NO. 9) (109-129), HTLV-II env-2 (SEQ. ID. NO. 15) (171-198) and HTLV-II gag-2 (SEQ. ID. NO. 23) (111-129). Additionally, peptides were prepared which were taken from the same antigenic region as the present peptides, but contain several fewer or more amino acid residues. These peptides correspond to HTLV-I gag-4 (103-116) (SEQ. ID. NO. 26), HTLV-II gag-1 (115-135) (SEQ. ID. NO. 28) and HTLV-II env-7 (186-195) (SEQ. ID. NO. 27). The data from these assays was tabulated in Table 3.

TABLE 3

Comparison Of Peptide Amino Acid Sequences And Serological Reactivities

| Protein | Amino Acids | HTLV-I Reactivity | HTLV-II Reactivity |
|---|---|---|---|
| HTLV-I gp46 | 190-213 | 4/14 | 0/14 |
| HTLV-I gp46 | 174-204 | 11/14 | 0/14 |
| HTLV-II gp46 | 186-195 | 0/14 | 0/14 |
| HTLV-II gp46 | 171-198 | 0/14 | 11/14 |
| HTLV-I p19 | 103-116 | 0/14 | 0/14 |
| HTLV-I p19 | 100-129 | 14/14 | 0/14 |
| HTLV-I p19 | 109-129 | 5/14 | 0/14 |
| HTLV-II p19 | 115-135 | 6/14 | 3/14 |
| HTLV-II p19 | 111-129 | 0/14 | 4/14 |

This data clearly demonstrates that the addition, or removal, of small numbers of amino acids to or from a peptide may significantly influence its ability to bind to an antibody, and the specificity with which it binds.

Example 6

Differentiation Of HTLV-I and HTLV-II With Prior Art Peptides

Immunoassays were conducted as in Examples 1 and 2, and applied to the same 28 member panel used in Example 3. Beads were coated with peptides disclosed in Blomberg, supra, and Vahlne, surra. The Vahlne peptides tested were HTLV-I "H" and "O" and HTLV-II "H" and "O". The Blomberg peptides tested were the four disclosed preferred peptides, 1GB, 2GB, 1EA and 2EA, in approximately the same region as the peptides of this disclosure. Each of the comparative methods were conducted according to the method of the present invention with the substitution of the prior art peptides. In the case of the commercially available SynthEIA, the assay was performed according to the manufacturer's recommended protocol. Results are tabulated in Table 4.

TABLE 4

Reactivity of Prior Art Peptides

| Peptide | Amino Acid | HTLV-I Reactivity | HTLV-II Reactivity |
|---|---|---|---|
| Vahlne HTLV-I "O" | HTLV-I 89–110 | 1/14 | 0/14 |

TABLE 4-continued

Reactivity of Prior Art Peptides

| Peptide | Amino Acid | HTLV-I Reactivity | HTLV-II Reactivity |
|---|---|---|---|
| Vahlne HTLV-I "H" | HTLV-I 176–199 | 8/14[1] | 0/14 |
| Vahlne HTLV-II "H" | HTLV-II 172–195 | 0/14 | 4/14 |
| Vahlne HTLV-II "0" | HTLV-II 85–106 | 0/14 | 6/14 |
| Blomberg "1GB" | HTLV-I 111–130 | 6/14[2] | 0/14 |
| Blomberg "2GB" | HTLV-II 117–136 | 6/14 | 4/14 |
| Blomberg "1EA" | HTLV-I 190–213 | 10/14 | 1/14 |
| Blomberg "2EA" | HTLV-II 186–209 | 1/14 | 3/14 |
| SynthEIA System | | 11/14 | 5/14[3] |

[1]1 sample was indeterminate
[2]1 sample was indeterminate
[3]1 additional HTLV-II sample was identified as HTLV-I Example 7

Differentiation Between HTLV-I And HTLV-II (Comparative)

The method of Examples 1 and 2 was used to investigate a panel of test samples which had been previously classified by PCR. The present invention was compared with the method of Blomberg. The Blomberg peptides tested were the four disclosed preferred peptides, 1GB, 2GB, 1EA and 2EA, which fall in approximately the same region as several of the peptides of the present invention. Each of these comparative methods were conducted according to the method of the present invention with the substitution of the prior art peptides. The results are shown in Table 5.

TABLE 5

Differentiation Of HTLV-I And HTLV-II (Comparative)

| | SEQ. ID. NO. | | | | Blomberg | | | |
|---|---|---|---|---|---|---|---|---|
| | 1 | 8 | 15 | 24 | 1EA | 1GB | 2EA | 2GB |
| HTLV-I | 48/50 | 49/50 | 1/50[2] | 4/50 | 43/50 | 36/50 | 1/50[2] | 24/50 |
| HTLV-II | 1/50[1] | 7/50 | 47/50 | 34/50 | 0/50 | 2/50 | 34/50 | 40/50 |

[2]This sample was strongly HTLV-I positive and borderline HTLV-II positive.
[1]This sample was strongly gp HTLV-II positive and borderline HTLV-I positive.

Of course, it should be understood that a wide range of changes and modifications may be made to the preferred embodiment described above. It is therefore intended that the foregoing detailed description be understood that it is the following claims, including all equivalents, which are intended to define the scope of this invention.

We claim:

1. A method for differentiating antibodies against HTLV-I from antibodies against HTLV-II in a test sample, comprising:
   a. determining the presence of antibodies against HTLV-I in said test sample, said determination comprising the steps of:
      i. forming a first mixture by contacting said test sample with a peptide consisting of the amino acid sequence corresponding to SEQ. ID. No. 1;
      ii. incubating said first mixture for a time and under conditions sufficient to form complexes between said peptide and said HTLV-I antibody;
      iii. contacting said complexes with an indicator reagent comprising a signal generating compound attached to an antihuman IgG antibody, to form a second mixture;
      iv. incubating said second mixture for a time and under conditions sufficient to form complexes comprising said peptide, said HTLV-1 antibody and said IgG antibody;
      v. determining the presence of antibodies against HTLV-I in said test sample by detecting signal generated by said signal generating compound;
   b. determining the presence of antibodies against HTLV-II in said test sample, said determination comprising:
      i. forming a first mixture by contacting said test sample with a peptide consisting of the amino acid sequence corresponding to SEQ. ID. No. 15;
      ii. incubating said first mixture for a time and under conditions sufficient to form complexes between said peptide and said HTLV-II antibody;
      iii. contacting said complexes with an indicator reagent comprising a signal generating compound attached to an antihuman IgG antibody, to form a second mixture;
      iv. incubating said second mixture for a time and under conditions sufficient to form complexes comprising said peptide, said HTLV-II antibody and said IgG antibody;
      v. determining the presence of antibodies against HTLV-II in said test sample by detecting signal generated by said signal generating compound;
   c. determining the pattern of reaction of said test sample for antibodies against HTLV-I and HTLV-II to distinguish between HTLV-II and HTLV-II infections.

2. The method of claim 1 wherein step (a)(i) further comprises contacting said test sample with at least one additional peptide selected from the group consisting of peptides consisting of the amino acid sequence corresponding to SEQ. ID NOS 3, 4, and 5.

3. The method of claim 2, wherein said additional peptide consists of the amino acid sequence corresponding to SEQ. ID. NO. 5.

4. The method of claim 2, wherein said test sample is contacted with said peptides concurrently.

5. The method of claim 4 wherein said peptides are coated on polystyrene beads.

6. The method of claim 4 wherein said peptides are coated on microparticle beads.

7. The method of claim 1 wherein step (b)(i) further comprises contacting said test sample with a peptide consisting of the amino acid sequence corresponding to SEQ. ID. NO. 22.

8. The method of claim 7, wherein said test sample is contacted with said peptides concurrently.

9. The method of claim 8 wherein said peptides are coated on polystyrene beads.

10. The method of claim 8 wherein said peptides are coated on microparticle beads.

11. An article of manufacture comprising:
    a first container comprising a peptide consisting of the amino acid sequence corresponding to SEQ. ID. NO. 1) and
    a second container comprising a peptide consisting of the amino acid sequence corresponding to SEQ. ID. NO. 15.

12. The article of claim 11, wherein said first container further comprises a peptide consisting of the amino acid sequence corresponding to SEQ. ID. NO. 5.

13. The article of claim 11, wherein said second container further comprises a peptide consisting of the amino acid sequence corresponding to SEQ. ID. NO. 22.

14. A method for differentiating antibodies against HTLV-I from antibodies against HTLV-II in a test sample, comprising:
    a. determining the presence of antibodies against HTLV-I in said test sample, said determination comprising the steps of:
       i. forming a first mixture by contacting said test sample with a peptide consisting of the amino acid sequence corresponding to SEQ. ID. No. 1;
       ii. incubating said fit mixture for a time and under conditions sufficient to form complexes between said peptide and said HTLV-I antibody;
       iii. forming a second mixture by contacting said complexes with an indicator reagent comprising a signal generating compound attached to a peptide antigen which can bind to said complexes formed in step (ii);
       iv. incubating said second mixture for a time and under conditions sufficient to form complexes comprising said peptide from step (i), said HTLV-I antibody and said peptide from step iii;
       v. determining the presence of antibodies against HTLV-I in said test sample by detecting signal generated by said signal generating compound;
    b. determining the presence of antibodies against HTLV-II in said test sample, said determination comprising:
       i. forming a first mixture by contacting said test sample with a peptide consisting of the amino acid sequence corresponding to SEQ. ID. No. 15;
       ii. incubating said first mixture for a time and under conditions sufficient to form complexes between said peptide and said HTLV-I antibody;
       iii. forming a second mixture by contacting said complexes with an indicator reagent comprising a signal generating compound attached to peptide antigen which can bind to said complexes formed in step ii;
       iv. incubating said second mixture for a time and under conditions sufficient to form complexes comprising said peptide from step (i), said HTLV-II antibody and said peptide from step iii;
       v. determining the presence of antibodies against HTLV-II in said test sample by detecting signal generated by said signal generating compound;
    c. determining the pattern of reaction of said test sample for antibodies against HTLV-I and HTLV-II to distinguish between HTLV-I and HTLV-II infections.

15. The method of claim 14 wherein step (a)(i) further comprises contacting said test sample with at least one peptide selected from the group consisting of peptides corresponding to SEQ. ID. NOS 3, 4, and 5.

16. The method of claim 14 wherein step (a)(i) further comprises contacting said test sample with a peptide corresponding to SEQ. ID NO. 22.

17. A method for differentiating antibodies against HTLV-I from antibodies against HTLV-II in a test sample, comprising:

a. determining the presence of antibodies against HTLV-I in said test sample, said determination comprising the steps of:
     i. forming a first mixture by contacting said test sample with at least one HTLV-I peptide selected from the group consisting of peptides corresponding to SEQ. ID. NOS. 1, 7, and 8;
     ii. incubating said first mixture for a time and under conditions sufficient to form complexes between said peptide and said HTLV-I antibody present in said sample;
     iii. forming a second mixture by contacting said complexes formed in step (ii) with an indicator reagent capable of binding with said complexes formed in step ii, and wherein said indicator reagent comprises a signal generating compound;
     iv. incubating said second mixture for a time and under conditions sufficient to form complexes comprising said peptide, said HTLV-I antibody and said indicator reagent;
     v. determining the presence of antibodies against HTLV-I in said test sample by detecting signal generated by said signal generating compound;
  b. determining the presence of antibodies against HTLV-II in said test sample, said determination comprising:
     i. forming a first mixture by contacting said test sample with at least one HTLV-II peptide selected from the group consisting of peptides corresponding to SEQ. ID. NOS. 15, 23, 24 and 25;
     ii. incubating said first mixture for a time and under conditions sufficient to form complexes between said peptide and HTLV-II antibody present in said sample;
     iii. forming a second mixture by contacting said complexes formed in step (ii) with an indicator reagent capable of binding with said complexes formed in step ii, and wherein said indicator reagent comprises a signal generating compound;
     iv. incubating said second mixture for a time and under conditions sufficient to form complexes comprising said peptide, said HTLV-I antibody and said indicator reagent;
     v. determining the presence of antibodies against HTLV-I in said test sample by detecting signal generated by said signal generating compound;
  c. determining the pattern of reaction of said test sample for antibodies against HTLV-I and HTLV-II to distinguish between HTLV-I and HTLV-II infections.

* * * * *

UNITED STATES PATENT AND TRADEMARK OFFICE
CERTIFICATE OF CORRECTION

PATENT NO. : 5,773,211
DATED : June 30, 1998
INVENTOR(S) : Shih et al.

It is certified that error appears in the above-identified patent and that said Letters Patent is hereby corrected as shown below:

Column 33, line 45, change "HTLV-II" to --HTLV-I--.

Column 34, line 5, change ")" to --,--.

Column 34, line 25, change "fit" to --first--.

Signed and Sealed this

First Day of December, 1998

*Attest:*

*Attesting Officer*

BRUCE LEHMAN
*Commissioner of Patents and Trademarks*

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
( A ) LENGTH: 31 amino acids
( B ) TYPE: amino acid (D) TOPOLOGY: linear (i i) MOLECULE TYPE: peptide (v) FRAGMENT TYPE: internal (v i i i) POSITION IN GENOME:
    (B) MAP POSITION: 174-204

(x i) SEQUENCE DESCRIPTION: SEQ ID NO:1:

```
Phe Leu Asn Thr Glu Pro Ser Gln Leu Pro Pro Thr Ala Pro Pro Leu
 1               5                  10                  15

Leu Pro His Ser Asn Leu Asp His Ile Leu Glu Pro Ser Ile Pro
             20                  25                  30
```

(2) INFORMATION FOR SEQ ID NO:2:

(i) SEQUENCE CHARACTERISTICS:
        (A) LENGTH: 34 amino acids
        (B) TYPE: amino acid
        (D) TOPOLOGY: linear (i i) MOLECULE TYPE: peptide (v) FRAGMENT TYPE: internal (v i i i) POSITION IN GENOME:
    (B) MAP POSITION: 180-213

(x i) SEQUENCE DESCRIPTION: SEQ ID NO:2:

```
Ser Gln Leu Pro Pro Thr Ala Pro Pro Leu Leu Pro His Ser Asn Leu
 1               5                  10                  15

Asp His Ile Leu Glu Pro Ser Ile Pro Trp Lys Ser Lys Leu Leu Thr
             20                  25                  30

Leu Val
```

(2) INFORMATION FOR SEQ ID NO:3:

(i) SEQUENCE CHARACTERISTICS:
        (A) LENGTH: 31 amino acids
        (B) TYPE: amino acid
        (D) TOPOLOGY: linear (i i) MOLECULE TYPE: peptide (v) FRAGMENT TYPE: internal (v i i i) POSITION IN GENOME:
    (B) MAP POSITION: 227-257

(x i) SEQUENCE DESCRIPTION: SEQ ID NO:3:

```
Cys Ile Asp Arg Ala Ser Leu Ser Thr Trp His Val Leu Tyr Ser Pro
 1               5                  10                  15

Asn Val Ser Val Pro Ser Ser Ser Thr Pro Leu Leu Tyr Pro
             20                  25                  30
```

(2) INFORMATION FOR SEQ ID NO:4:

(i) SEQUENCE CHARACTERISTICS:
        (A) LENGTH: 31 amino acids
        (B) TYPE: amino acid
        (D) TOPOLOGY: linear (i i) MOLECULE TYPE: peptide (v) FRAGMENT TYPE: internal (v i i i) POSITION IN GENOME:
    (B) MAP POSITION: 230-260

( x i ) SEQUENCE DESCRIPTION: SEQ ID NO:4:

Arg Ala Ser Leu Ser Thr Trp His Val Leu Tyr Ser Pro Asn Val Ser
1               5                   10                  15

Val Pro Ser Ser Ser Ser Thr Pro Leu Leu Tyr Pro Ser Leu Ala
            20                  25                  30

( 2 ) INFORMATION FOR SEQ ID NO:5:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( v ) FRAGMENT TYPE: internal ( v i i i ) POSITION IN GENOME:
        ( B ) MAP POSITION: 237-260

( x i ) SEQUENCE DESCRIPTION: SEQ ID NO:5:

His Val Leu Tyr Ser Pro Asn Val Ser Val Pro Ser Ser Ser Ser Thr
1               5                   10                  15

Pro Leu Leu Tyr Pro Ser Leu Ala
            20

( 2 ) INFORMATION FOR SEQ ID NO:6:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( v ) FRAGMENT TYPE: internal ( v i i i ) POSITION IN GENOME:
        ( B ) MAP POSITION: 190-213

( x i ) SEQUENCE DESCRIPTION: SEQ ID NO:6:

Leu Pro His Ser Asn Leu Asp His Ile Leu Glu Pro Ser Ile Pro Trp
1               5                   10                  15

Lys Ser Lys Leu Leu Thr Leu Val
            20

( 2 ) INFORMATION FOR SEQ ID NO:7:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( v ) FRAGMENT TYPE: internal ( v i i i ) POSITION IN GENOME:
        ( B ) MAP POSITION: 100-129

( x i ) SEQUENCE DESCRIPTION: SEQ ID NO:7:

Pro Pro Pro Ser Ser Pro Thr His Asp Pro Pro Asp Ser Asp Pro Gln
1               5                   10                  15

Ile Pro Pro Pro Tyr Val Glu Pro Thr Ala Pro Gln Val Leu
            20                  25                  30

( 2 ) INFORMATION FOR SEQ ID NO:8:

( i ) SEQUENCE CHARACTERISTICS:
   ( A ) LENGTH: 26 amino acids
   ( B ) TYPE: amino acid
   ( D ) TOPOLOGY: linear ( i i ) MOLECULE TYPE: peptide ( v ) FRAGMENT TYPE: internal ( v i i i ) POSITION IN GENOME:
   ( B ) MAP POSITION: 104-129

( x i ) SEQUENCE DESCRIPTION: SEQ ID NO:8:

Ser Pro Thr His Asp Pro Pro Asp Ser Asp Pro Gln Ile Pro Pro
1               5                   10                  15
Tyr Val Glu Pro Thr Ala Pro Gln Val Leu
            20                  25

( 2 ) INFORMATION FOR SEQ ID NO:9:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: peptide ( v ) FRAGMENT TYPE: internal ( v i i i ) POSITION IN GENOME:
   ( B ) MAP POSITION: 109-129

( x i ) SEQUENCE DESCRIPTION: SEQ ID NO:9:

Pro Pro Asp Ser Asp Pro Gln Ile Pro Pro Pro Tyr Val Glu Pro Thr
1               5                   10                  15
Ala Pro Gln Val Leu
            20

( 2 ) INFORMATION FOR SEQ ID NO:10:

( i ) SEQUENCE CHARACTERISTICS:
      ( A ) LENGTH: 20 amino acids
      ( B ) TYPE: amino acid
      ( D ) TOPOLOGY: linear ( i i ) MOLECULE TYPE: peptide ( v ) FRAGMENT TYPE: internal ( v i i i ) POSITION IN GENOME:
   ( B ) MAP POSITION: 100-119

( x i ) SEQUENCE DESCRIPTION: SEQ ID NO:10:

Pro Pro Pro Ser Ser Pro Thr His Asp Pro Asp Ser Asp Pro Gln
1               5                   10                  15
Ile Pro Pro Pro
            20

( 2 ) INFORMATION FOR SEQ ID NO:11:

( i ) SEQUENCE CHARACTERISTICS:
      ( A ) LENGTH: 28 amino acids
      ( B ) TYPE: amino acid
      ( D ) TOPOLOGY: linear ( i i ) MOLECULE TYPE: peptide ( v ) FRAGMENT TYPE: internal ( v i i i ) POSITION IN GENOME:
   ( B ) MAP POSITION: 100-127

( x i ) SEQUENCE DESCRIPTION: SEQ ID NO:11:

Pro Pro Pro Ser Ser Pro Thr His Asp Pro Pro Asp Ser Asp Pro Gln
1               5                       10                      15

Ile Pro Pro Pro Tyr Val Glu Pro Thr Ala Pro Gln
                20                  25

( 2 ) INFORMATION FOR SEQ ID NO:12:

( i ) SEQUENCE CHARACTERISTICS:
      ( A ) LENGTH: 27 amino acids
      ( B ) TYPE: amino acid
      ( D ) TOPOLOGY: linear ( i i ) MOLECULE TYPE: peptide ( v ) FRAGMENT TYPE: internal ( v i i i ) POSITION IN GENOME:
      ( B ) MAP POSITION: 100-126

( x i ) SEQUENCE DESCRIPTION: SEQ ID NO:12:

Pro Pro Pro Ser Ser Pro Thr His Asp Pro Pro Asp Ser Asp Pro Gln
1               5                       10                      15

Ile Pro Pro Pro Tyr Val Glu Pro Thr Ala Pro
                20                  25

( 2 ) INFORMATION FOR SEQ ID NO:13:

( i ) SEQUENCE CHARACTERISTICS:
      ( A ) LENGTH: 32 amino acids
      ( B ) TYPE: amino acid
      ( D ) TOPOLOGY: linear ( i i ) MOLECULE TYPE: peptide ( v ) FRAGMENT TYPE: internal ( v i i i ) POSITION IN GENOME:
      ( B ) MAP POSITION: 167-198

( x i ) SEQUENCE DESCRIPTION: SEQ ID NO:13:

Pro Leu Trp Phe Ile Thr Ser Glu Pro Thr Gln Pro Pro Pro Thr Ser
1               5                       10                      15

Pro Pro Leu Val His Asp Ser Asp Leu Glu His Val Leu Thr Pro Ser
                20                  25                  30

( 2 ) INFORMATION FOR SEQ ID NO:14:

( i ) SEQUENCE CHARACTERISTICS:
      ( A ) LENGTH: 32 amino acids
      ( B ) TYPE: amino acid
      ( D ) TOPOLOGY: linear ( i i ) MOLECULE TYPE: peptide ( v ) FRAGMENT TYPE: internal ( v i i i ) POSITION IN GENOME:
      ( B ) MAP POSITION: 167-198

( x i ) SEQUENCE DESCRIPTION: SEQ ID NO:14:

Pro Leu Trp Phe Ile Thr Ser Glu Pro Thr Gln Pro Pro Pro Thr Pro
1               5                       10                      15

Pro Pro Leu Val His Asp Ser Asp Leu Glu His Val Leu Thr Pro Ser
                20                  25                  30

( 2 ) INFORMATION FOR SEQ ID NO:15:

( i ) SEQUENCE CHARACTERISTICS:
  ( A ) LENGTH: 28 amino acids
  ( B ) TYPE: amino acid
  ( D ) TOPOLOGY: linear ( i i ) MOLECULE TYPE: peptide ( v ) FRAGMENT TYPE: internal ( v i i i ) POSITION IN GENOME:
  ( B ) MAP POSITION: 171-198

( x i ) SEQUENCE DESCRIPTION: SEQ ID NO:15:

```
Ile Thr Ser Glu Pro Thr Gln Pro Pro Pro Thr Ser Pro Pro Leu Val
1               5                   10                  15
His Asp Ser Asp Leu Glu His Val Leu Thr Pro Ser
            20                  25
```

( 2 ) INFORMATION FOR SEQ ID NO:16:

( i ) SEQUENCE CHARACTERISTICS:
  ( A ) LENGTH: 28 amino acids
  ( B ) TYPE: amino acid
  ( D ) TOPOLOGY: linear ( i i ) MOLECULE TYPE: peptide ( v ) FRAGMENT TYPE: internal ( v i i i ) POSITION IN GENOME:
  ( B ) MAP POSITION: 171-198

( x i ) SEQUENCE DESCRIPTION: SEQ ID NO:16:

```
Ile Thr Ser Glu Pro Thr Gln Pro Pro Pro Thr Pro Pro Pro Leu Val
1               5                   10                  15
His Asp Ser Asp Leu Glu His Val Leu Thr Pro Ser
            20                  25
```

( 2 ) INFORMATION FOR SEQ ID NO:17:

( i ) SEQUENCE CHARACTERISTICS:
  ( A ) LENGTH: 28 amino acids
  ( B ) TYPE: amino acid
  ( D ) TOPOLOGY: linear ( i i ) MOLECULE TYPE: peptide ( v ) FRAGMENT TYPE: internal ( v i i i ) POSITION IN GENOME:
  ( B ) MAP POSITION: 173-200

( x i ) SEQUENCE DESCRIPTION: SEQ ID NO:17:

```
Ser Glu Pro Thr Gln Pro Pro Pro Thr Ser Pro Pro Leu Val His Asp
1               5                   10                  15
Ser Asp Leu Glu His Val Leu Thr Pro Ser Thr Ser
            20                  25
```

( 2 ) INFORMATION FOR SEQ ID NO:18:

( i ) SEQUENCE CHARACTERISTICS:
  ( A ) LENGTH: 32 amino acids
  ( B ) TYPE: amino acid
  ( D ) TOPOLOGY: linear ( i i ) MOLECULE TYPE: peptide ( v ) FRAGMENT TYPE: internal ( v i i i ) POSITION IN GENOME:

(B) MAP POSITION: 173-204

(xi) SEQUENCE DESCRIPTION: SEQ ID NO:18:

```
Ser Glu Pro Thr Gln Pro Pro Pro Thr Ser Pro Pro Leu Val His Asp
 1               5                  10                  15
Ser Asp Leu Glu His Val Leu Thr Pro Ser Thr Ser Trp Thr Thr Lys
                20                  25                  30
```

(2) INFORMATION FOR SEQ ID NO:19:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (v) FRAGMENT TYPE: internal (viii) POSITION IN GENOME:
        (B) MAP POSITION: 176-209

(xi) SEQUENCE DESCRIPTION: SEQ ID NO:19:

```
Thr Gln Pro Pro Pro Thr Ser Pro Pro Leu Val His Asp Ser Asp Leu
 1               5                  10                  15
Glu His Val Leu Thr Pro Ser Thr Ser Trp Thr Thr Lys Ile Leu Lys
                20                  25                  30
Phe Ile
```

(2) INFORMATION FOR SEQ ID NO:20:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (v) FRAGMENT TYPE: internal (viii) POSITION IN GENOME:
        (B) MAP POSITION: 176-209

(xi) SEQUENCE DESCRIPTION: SEQ ID NO:20:

```
Thr Arg Pro Pro Pro Thr Pro Pro Pro Leu Val His Asp Ser Asp Leu
 1               5                  10                  15
Glu His Val Leu Thr Pro Ser Thr Ser Trp Thr Thr Lys Met Leu Lys
                20                  25                  30
Phe Ile
```

(2) INFORMATION FOR SEQ ID NO:21:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (v) FRAGMENT TYPE: internal (viii) POSITION IN GENOME:
        (B) MAP POSITION: 228-257

(xi) SEQUENCE DESCRIPTION: SEQ ID NO:21:

```
Ser Leu Ser Ser Trp His Val Leu Tyr Thr Pro Asn Ile Ser Ile Pro
 1               5                  10                  15
```

```
         Gln  Gln  Thr  Ser  Ser  Arg  Thr  Ile  Leu  Phe  Pro  Ser  Leu  Ala
                        20                  25                       30
```

( 2 ) INFORMATION FOR SEQ ID NO:22:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( v ) FRAGMENT TYPE: internal ( v i i i ) POSITION IN GENOME:
        ( B ) MAP POSITION: 83-108

( x i ) SEQUENCE DESCRIPTION: SEQ ID NO:22:

```
         Trp  Ile  Lys  Lys  Pro  Asn  Arg  Gln  Gly  Leu  Gly  Tyr  Tyr  Ser  Pro  Ser
         1                   5                       10                      15

Tyr  Asn  Asp  Pro  Cys  Ser  Leu  Gln  Cys  Pro
                        20                  25
```

( 2 ) INFORMATION FOR SEQ ID NO:23:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( v ) FRAGMENT TYPE: internal ( v i i i ) POSITION IN GENOME:
        ( B ) MAP POSITION: 111-129

( x i ) SEQUENCE DESCRIPTION: SEQ ID NO:23:

```
         Pro  Pro  Pro  Pro  Pro  Pro  Ser  Pro  Glu  Ala  His  Val  Pro  Pro  Pro  Tyr
         1                   5                       10                      15

Val  Glu  Pro
```

( 2 ) INFORMATION FOR SEQ ID NO:24:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( v ) FRAGMENT TYPE: internal ( v i i i ) POSITION IN GENOME:
        ( B ) MAP POSITION: 109-127

( x i ) SEQUENCE DESCRIPTION: SEQ ID NO:24:

```
         Thr  Pro  Pro  Pro  Pro  Pro  Pro  Pro  Ser  Pro  Glu  Ala  His  Val  Pro  Pro
         1                   5                       10                      15

Pro  Tyr  Val
```

( 2 ) INFORMATION FOR SEQ ID NO:25:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide (v) FRAGMENT TYPE: internal (viii) POSITION IN GENOME:
(B) MAP POSITION: 107-125

(xi) SEQUENCE DESCRIPTION: SEQ ID NO:25:

Thr Thr Thr Pro Pro Pro Pro Pro Pro Pro Ser Pro Glu Ala His Val
1               5                   10                  15

Pro Pro Pro (2) INFORMATION FOR SEQ ID NO:26:

(i) SEQUENCE CHARACTERISTICS:
(A) LENGTH: 14 amino acids
(B) TYPE: amino acid
(D) TOPOLOGY: linear (ii) MOLECULE TYPE: peptide (v) FRAGMENT TYPE: internal (viii) POSITION IN GENOME:
(B) MAP POSITION: 103-116

(xi) SEQUENCE DESCRIPTION: SEQ ID NO:26:

Ser Ser Pro Thr His Asp Pro Pro Asp Ser Asp Pro Gln Ile
1               5                   10

(2) INFORMATION FOR SEQ ID NO:27:

(i) SEQUENCE CHARACTERISTICS:
(A) LENGTH: 10 amino acids
(B) TYPE: amino acid
(D) TOPOLOGY: linear (ii) MOLECULE TYPE: peptide (v) FRAGMENT TYPE: internal (viii) POSITION IN GENOME:
(B) MAP POSITION: 186-195

(xi) SEQUENCE DESCRIPTION: SEQ ID NO:27:

Val His Asp Ser Asp Leu Glu His Val Leu
1               5                   10

(2) INFORMATION FOR SEQ ID NO:28:

(i) SEQUENCE CHARACTERISTICS:
(A) LENGTH: 21 amino acids
(B) TYPE: amino acid
(D) TOPOLOGY: linear (ii) MOLECULE TYPE: peptide (v) FRAGMENT TYPE: internal (viii) POSITION IN GENOME:
(B) MAP POSITION: 115-135

(xi) SEQUENCE DESCRIPTION: SEQ ID NO:28:

Pro Pro Ser Pro Glu Ala His Val Pro Pro Pro Tyr Val Glu Pro Thr
1               5                   10                  15

Thr Thr Gln Cys Phe
            20